United States Patent [19]

Chevallet

[11] Patent Number: 5,366,630
[45] Date of Patent: Nov. 22, 1994

[54] ARTIFICIAL KIDNEY AND A METHOD OF CONTROLLING IT

[75] Inventor: Jacques Chevallet, Serezin du Rhone, France

[73] Assignee: Hospal Industrie, Meyzieu Cedex, France

[21] Appl. No.: 917,408

[22] Filed: Jul. 23, 1992

[30] Foreign Application Priority Data

Aug. 14, 1991 [FR] France .................. 91 10463

[51] Int. Cl.⁵ .............................. B01D 61/00
[52] U.S. Cl. ..................... 210/645; 210/85; 210/86; 210/90; 210/97; 210/138; 210/195.2; 210/321.65; 210/321.72; 210/646; 210/650; 210/739; 210/741; 210/929; 604/4
[58] Field of Search ................... 210/85, 86, 89, 90, 210/97, 98, 134, 138, 143, 195.2, 258, 321.6, 321.65, 321.72, 321.75, 321.84, 645, 646, 650, 739, 741, 805, 744, 929; 604/4, 5, 6

[56] References Cited

U.S. PATENT DOCUMENTS

| 4,204,957 | 5/1980 | Weickhardt | 210/98 |
| 4,606,826 | 8/1986 | Sano et al. | 210/646 |
| 4,708,802 | 11/1987 | Rath et al. | 210/641 |
| 4,711,715 | 12/1987 | Polaschegg | 210/103 |
| 4,735,727 | 4/1988 | Heitmeier et al. | 210/929 |
| 4,769,132 | 9/1988 | Patono | 210/86 |
| 4,844,810 | 7/1989 | Richalley et al. | 210/321.72 |
| 5,211,849 | 5/1993 | Kitaevich et al. | 210/645 |

FOREIGN PATENT DOCUMENTS

| 0122604 | 10/1984 | European Pat. Off. . |
| 0212127 | 3/1987 | European Pat. Off. . |
| 0256956 | 2/1988 | European Pat. Off. . |

Primary Examiner—Robert A. Dawson
Assistant Examiner—Sun Uk Kim
Attorney, Agent, or Firm—Finnegan, Henderson, Farabow, Garrett & Dunner

[57] ABSTRACT

The artificial kidney includes an exchanger having two compartments separated by a semipermeable membrane, the first compartment of which is connected to a circuit for conveying a flow of blood outside the body. A source of treatment liquid is provided, and a control unit selectively connects the source to either the inlet of the second compartment of the exchanger or to the blood circuit as a function of the transmembrane pressure. This kidney provides optimum purification treatment for patients suffering from temporary kidney failure.

23 Claims, 2 Drawing Sheets

ARTIFICIAL KIDNEY AND A METHOD OF CONTROLLING IT

BACKGROUND OF THE INVENTION

1. Field of the Invention

The present invention relates to an artificial kidney, and more particularly to an artificial kidney for treating people who are temporarily deprived of the use of their own kidneys following an accident or a surgical operation,

2. Description of the Related Art

Given the general state of weakness in which such patients are found, they cannot be subjected to the same intensive treatment as is given to patients suffering permanent kidney failure: i.e., a twice-weekly four-hour conventional hemodialysis or hemofiltration session. The rapid change in internal liquid balances that occurs in a traditional treatment approach places the cardiovascular system under intense stress that patients leaving the operating theater are generally not fit to withstand.

It is therefore the practice to purify the blood of such patients and to eliminate a portion of the water that accumulates in their tissues by using treatments that are not very intense but that are continuous, which treatments are easily tolerated by the body since there are no sudden changes, and are acceptable for people who are in no condition to move about.

Conventionally, the above-mentioned patients are subjected to two types of treatment: continuous hemofiltration and continuous hemodialysis.

Hemofiltration is based on removing from blood a portion of the impurity-containing plasma water therefrom by ultrafiltration through a semipermeable membrane. The transfer is driven by the pressure difference across the membrane. A substitution liquid may simultaneously be perfused into the patient, generally in smaller quantities than the filtrate that is removed, with the difference corresponding to the weight that it appears appropriate for the patient to loose. The ultrafiltration throughput, i.e. the efficiency of the hemofiltration treatment, is limited both by the characteristics of the filter (essentially the nature and the area of the membrane), and by the rate of flow of blood through the filter, which rate of flow is relatively low during continuous treatment (4 to 12 liters per hour as compared with 12 to 21 liters per hour during the treatment of patients with a permanent loss of kidney function).

During hemodialysis treatment, impurities in the blood are not entrained by convection in a flow of plasma water passing through a semipermeable membrane, as is the case in hemofiltration, but instead are diffused through a semipermeable membrane whose face that is not immersed in blood is irrigated by a flow of dialysis liquid that is free of the substances to be removed. Transfer is then driven by the concentration differences across the membrane.

For a given type of high permeability filter, for the same blood flow rate, and for an appropriate choice of dialysis liquid flow rate, it is possible to obtain much more effective purification of low molecular weight impurities with hemodialysis than it is with hemofiltration. In contrast, in addition to eliminating a portion of the water that accumulates in tissue, hemofiltration also makes it possible to eliminate impurities of high molecular weight that migrate little or not at all by diffusion.

From the above, it will be understood that to purify efficiently the blood of a patient suffering from kidney failure it is desirable to subject the patient to both treatment by hemofiltration and by hemodialysis.

European patent number 0 256 956 describes an artificial kidney enabling these treatments to be performed in alternation or simultaneously. That kidney includes an exchanger having two compartments that are separated by a semipermeable membrane. A first compartment is connected to a circuit for blood flow outside the body. The second compartment has an inlet that is connectable via a three-port valve to a first container of sterile dialysis liquid, and an outlet connected to a second container for collecting the waste dialysis liquid and the blood filtrate. The three-port valve also serves to connect the first container to the blood circuit downstream from the exchanger, with the sterile dialysis liquid being usable as an injectable substitution liquid. The sterile liquid may flow spontaneously or it may be driven by pumps, and the same applies to extracting the filtrate or the waste dialysis liquid.

With that artificial kidney, the method of treatment is selected manually by operating the three-port valve, on the prescription of the doctor.

SUMMARY OF THE INVENTION

An object of the invention is to provide an artificial kidney of that type but in which the method of treatment is selected automatically so as to ensure maximum purification of the patient given the doctor's prescriptions.

According to the present invention, this object is achieved by an artificial kidney comprising:
- a circuit for conveying a flow of blood outside the body, said circuit being connectable to a source of sterile liquid,
- an exchanger having two compartments separated by a semipermeable membrane, a first compartment being connected to the circuit for conveying blood outside the body, a second compartment having an inlet connectable to a source of sterile liquid,
- means for establishing a positive transmembrane pressure between the first and second compartments of the exchanger,
- means for measuring a value representative of the transmembrane pressure in the exchanger, and
- control means for causing a source of sterile liquid to be connected to the inlet of the second compartment of the exchanger when said measured value is greater than a predetermined threshold value.

According to a characteristic of the invention, the control means are also designed to connect a source of sterile liquid to the circuit for conveying a flow of blood outside the body when the measured value is less than a second predetermined threshold value, which is lower than the first threshold value.

According to another characteristic of the invention, the control means are also designed to alternate in a timing sequence between connecting a source of sterile liquid to the inlet of the second compartment of the exchanger and connecting a source of sterile liquid to the circuit for conveying a flow of blood outside the body.

Another object of the invention is to provide a method for controlling an artificial kidney of the above type, the method comprising the steps of:
measuring a value representative of the transmembrane pressure in the exchanger, comparing said value with a predetermined threshold value; and causing a source of sterile liquid to be connected to the inlet of the second compartment of the exchanger when the measured value is greater than the predetermined threshold value.

According to a variant of the invention, the method further comprises the step of:

comparing the measured value representative of the transmembrane pressure with a second predetermined threshold value, said second threshold value being less than the first threshold value; and causing a source of sterile liquid to be connected to the circuit for conveying a flow of blood outside the body when the measured value is less than the second threshold value.

According to another variant of the invention, the method further comprises the step, when the measured value has reached the predetermined threshold value, of alternating, in a timing sequence, the connection of a source of sterile liquid to the inlet of the second compartment of the exchanger and to the circuit for conveying a flow of blood outside the body.

BRIEF DESCRIPTION OF THE DRAWINGS

Other characteristics and advantages of the invention appear on reading the following description. Reference is made to the accompanying drawings, in which.

DETAILED DESCRIPTION OF THE PREFERRED EMBODIMENTS

Figure 1:
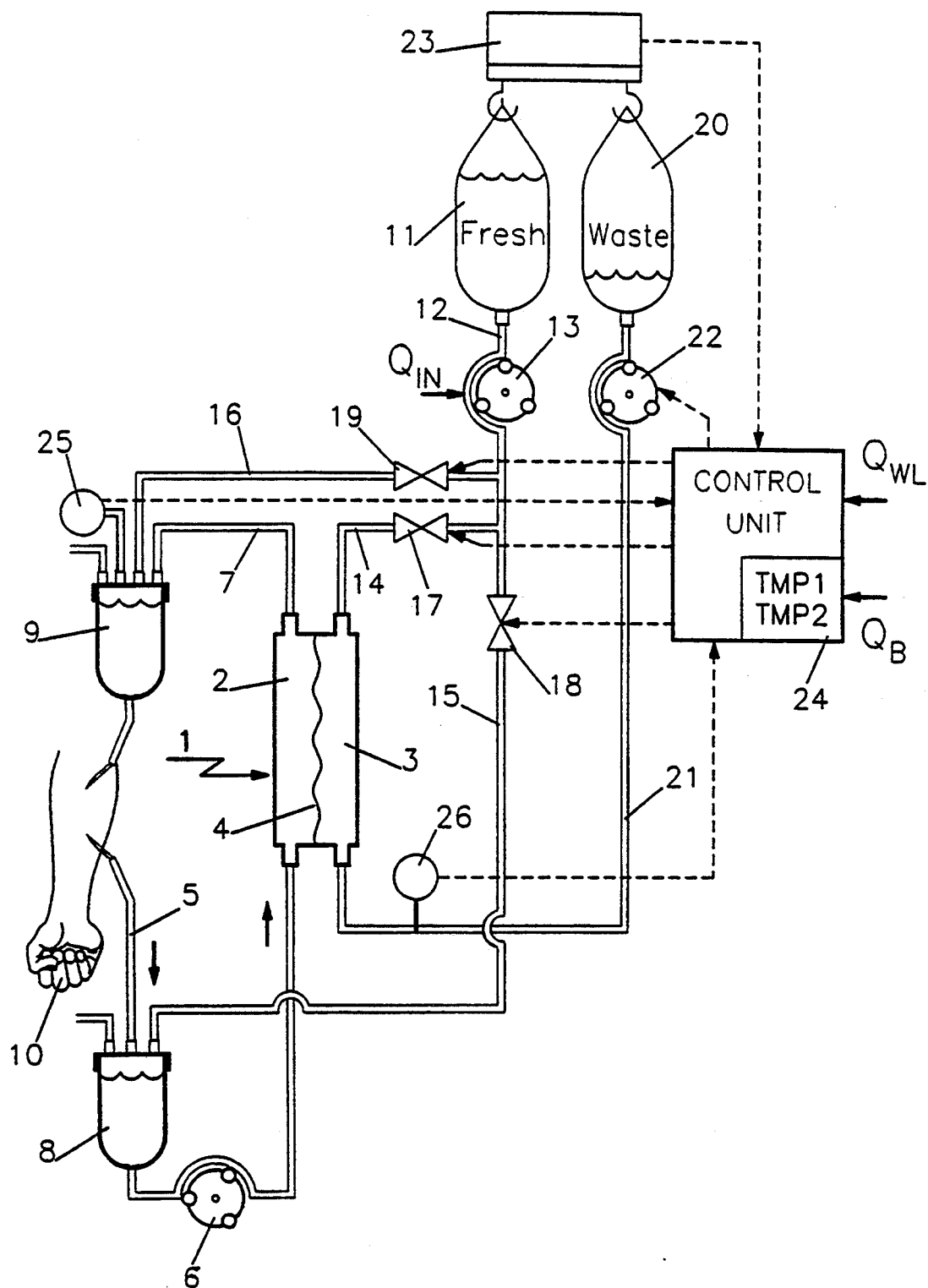
FIG. 1 is a simplified schematic diagram of a first embodiment of an artificial kidney of the invention.

In FIG. 1, an artificial kidney of the invention includes an exchanger 1 having two compartments 2 and 3 that are separated by a semipermeable membrane 4. The compartment 2 is connected to a circuit for conveying a flow of blood outside the body comprising an upstream duct 5 having a circulation pump 6 disposed therein, and a downstream duct 7. Each of these ducts 5 and 7 is provided with a respective bubble trap 8 or 9 and their free ends are fitted with respective needles or catheter connectors to enable them to be connected to the vascular circuit of a patient 10.

A first container 11 for sterile substitution/dialysis liquid is connected, via a length of common duct 12 including a circulation pump 13, to three ducts 14, 15, and 16 that are respectively connected to an inlet of the compartment 3 of the exchanger 1, to the upstream bubble trap 8, and to the downstream bubble trap 9. Respective blocking means 17, 18, and 19 such as electromagnetic clamps are disposed on the ducts 14, 15, and 16 so as to enable the container 11 to be connected selectively to one or other of them.

A second container 20 for collecting waste liquid (blood filtrate and/or waste dialysis liquid) is connected to an outlet of compartment 3 of the exchanger 1 by a duct 21 which includes means constituted by an extraction pump 22 for establishing variable suction inside the compartment 3.

The two containers 11 and 20 are connected to means 23 such as scales to measure the sterile and waste liquids and to deliver a signal to a control unit 24. The control unit also receives signals delivered by two pressure sensors 25 and 26 disposed respectively on the blood circuit downstream from the exchanger 1 and on the waste liquid circuit between the exchanger 1 and the extraction pump 22. On the basis of these measured weights and pressures and on the basis of a reference weight loss rate $Q_{WL}$ corresponding to equilibrium or to a desired unbalance between the sterile and waste liquids, the control unit 24 operates in a manner explained below to control the opening and closing of the clamps 17 and 19 and the flow rate of the pump 22, with the flow rate of the pump 13 being otherwise adjusted to a fixed value.

Before describing the operation of this kidney, it is necessary to add briefly to the above summary of hemofiltration. The flow rate of an ultrafiltrate through an exchanger is a function of the pressure difference (or transmembrane pressure) that exists between the two compartments of the exchanger, and this flow rate is limited both by the flow rate of blood through the exchanger and by the area and nature of the membrane which may be permeable to a greater or lesser extent. It is not possible to extract more than one-third of the plasma water from blood without running the risk of clogging up the exchanger with blood that is too concentrated. In addition to these two limiting factors, there is a third that relates to the very nature of blood. It is observed that for a membrane of given nature and for a given flow rate of blood through the exchanger, above a certain value of transmembrane pressure the ultrafiltration rate tends quickly to a substantially constant value. This phenomenon is due to the fact that under the effect of plasma convection caused by the transmembrane pressure, plasma proteins accumulate in the vicinity of the membrane and give rise to an osmotic pressure that limits the transmembrane pressure.

In light of the above, the artificial kidney of the invention operates on the following principles. A patient who has just lost kidney function is initially treated by hemofiltration. The sterile liquid contained in the container 11 is then used as a substitution liquid which is perfused into the patient. If at the beginning or during the session, the purification rate is observed to be insufficient, the doctor then increases the transmembrane pressure within the exchanger (by means of a command explained below in detail) so that the pressure becomes greater than a threshold value corresponding substantially to the maximum ultrafiltration rate, then the kidney automatically begins to operate in hemodialysis mode with the sterile liquid from the container 11 then being used as a dialysis liquid and flowing through the exchanger 1.

In greater detail, the artificial kidney of the invention operates as follows. Before the beginning of a treatment session, an operator stores in the memory of the control unit both a desired reference blood flow rate $Q_B$ and a desired weight loss rate $Q_{WL}$ as prescribed by the doctor (where $Q_{WL}$ is equal by definition to the desired difference at any instant between the ultrafiltration flow rate and the substitution liquid flow rate). In accordance with a correspondence relationship previously stored in its memory, the control unit 24 automatically associates the blood flow rate value $Q_B$ with an upper threshold value $TMP_1$ and a lower threshold value $TMP_2$ for the transmembrane pressure specific to the exchanger 1 being used. $TMP_1$ advantageously corresponds to the transmembrane pressure beyond which the ultrafiltration flow rate remains substantially constant at the selected blood flow rate $Q_B$ After initial rinsing and filling of the ducts and after the circuit for conveying a flow of blood outside the body has been connected to the vascular circuit of the patient 10, the pumps 6 and 13 are adjusted to constant flow rates.

Two situations can then arise depending on whether the blood of the patient 10 is to be subjected to purification, that is moderate or that is more intense. For moderate purification the flow rate $Q_{IN}$ of the sterile liquid pump 13 is selected to be less than the ultrafiltration flow rate corresponding to $TMP_1$ minus the weight loss flow rate $Q_{WL}$. Since the result of the comparisons performed by the control unit 24 between $TMP_1$ and the transmembrane pressure in the exchanger 1 as measured from the data delivered by the pressure sensors 25 and 26 indicates that $TMP_1$ is the greater, the control unit keeps the clamps 17 and 18 closed and the clamp 19 open: the kidney operates in hemofiltration mode, the sterile liquid contained in the container 11 is perfused into the patient, and the filtrate extracted in the exchanger 1 by the suction established in the compartment 3 by the pump 22 fills the second container 20. The pump 22 is controlled by the control unit 24 on a permanent basis as a function of the data provided by the scales 23 so that the real weight loss rate is equal to the desired weight loss rate $Q_{WL}$.

If the doctor judges that the blood of the patient 10 is being purified too slowly with the initially selected flow rate $Q_{IN}$, this flow rate must be increased. If the flow rate $Q_{IN}$ is increased so that it becomes greater than or equal to the ultrafiltration flow rate corresponding to $TMP_1$ minus the weight loss flow rate $Q_{WL}$, then the transmembrane pressure measured in the exchanger 1 becomes greater than or equal to $TMP_1$ and the control unit 24 then causes the clamp 19 to close while simultaneously opening the clamp 17, with the clamp 18 remaining closed. The kidney then operates in "hemodiafiltration" mode in which the effects of dialysis are combined with those of ultrafiltration, and the sterile liquid contained in the first container 11 then flows into the compartment 3 of the exchanger 1 into which plasma water continues to migrate by ultrafiltration. Opening the clamp 17 causes liquid to flow into the compartment 3 of the exchanger 1 and the transmembrane pressure to drop. When the transmembrane pressure reaches the level $TMP_2$, then the control unit 24 changes over the positions of the clamps 17 and 19 and the kidney returns to hemofiltration mode until the transmembrane pressure again reaches the level $TMP_1$, and so on.

In the kidney of the invention, the blood of a patient is thus purified rapidly by alternating phases of hemofiltration and of hemodiafiltration, with the frequency of the alternation being adjustable by an appropriate choice of $TMP_2$.

Figure 2:
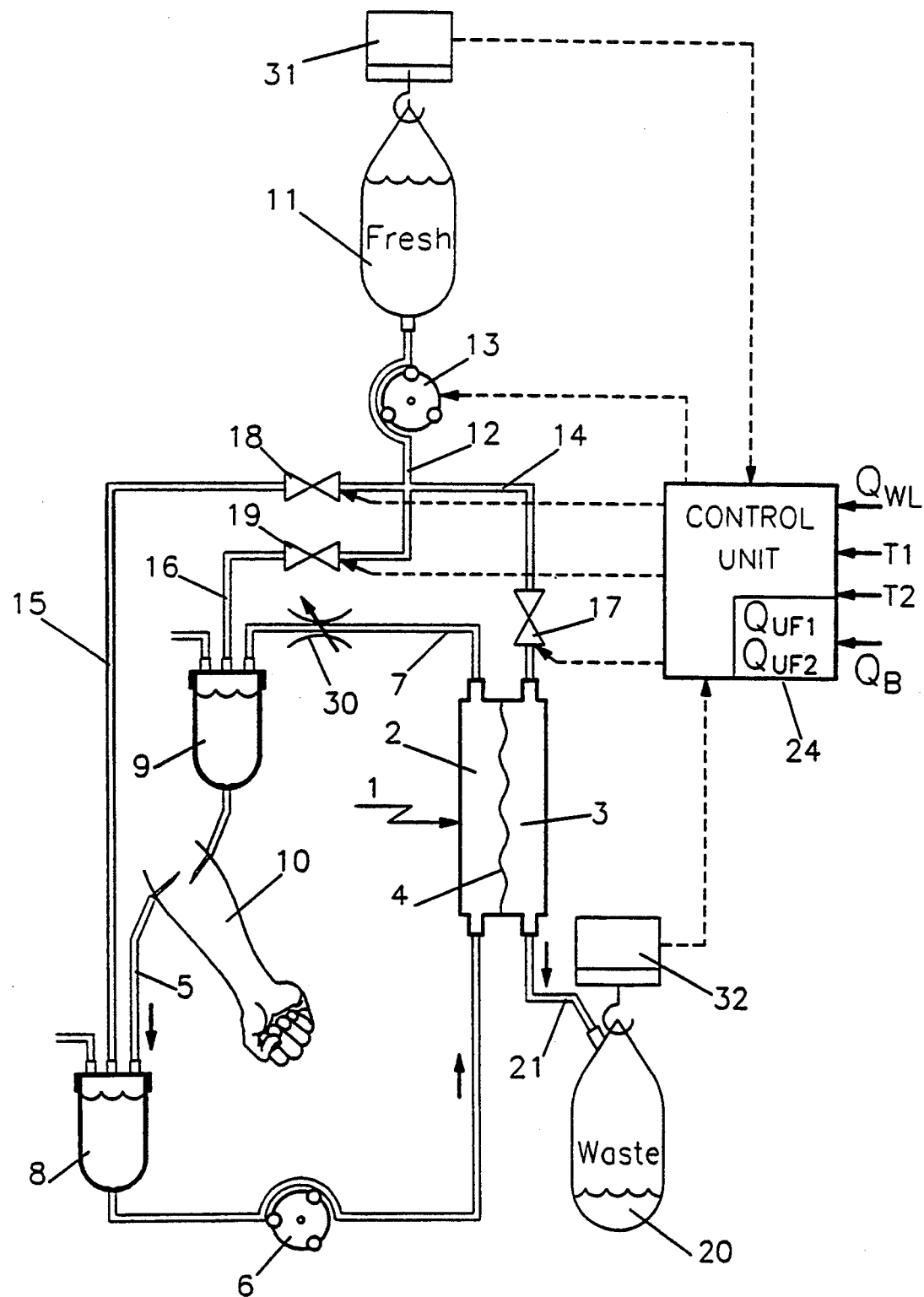
FIG. 2 is a simplified schematic diagram of a second embodiment of an artificial kidney of the invention.

FIG. 2 shows a second embodiment of the invention having in common with the preceding embodiment both its circuit for conveying a flow of blood outside the body and its circuits for sterile and waste liquids. It differs therefrom in that the means for establishing a variable transmembrane pressure in the exchanger 1 are constituted by an adjustable throttle member 30 disposed on the downstream duct 7 of the circuit for conveying blood outside the body. The transmembrane pressure thus results from an increase in pressure in the compartment 2 instead of from a decrease in pressure in the compartment 3, and the waste liquid circuit does not include an extraction pump.

In addition, the containers 11 and 20 are suspended from two independent scales 31 and 32. The transmembrane pressure in the exchanger 1 can thus be measured indirectly by measuring the ultrafiltration flow rate by means of the scales 31 and 32 (the scales 31 on their own in hemofiltration mode, the scales 31 and 32 in hemodiafiltration mode), and it is no longer necessary to measure the pressure in each of the compartments 2 and 3 of the exchanger 1 to determine the transmembrane pressure. That is why the threshold values that are automatically associated in the control unit 24 with the reference blood flow rate value $Q_B$ and which are used as references for switching from one treatment mode to the other are now ultrafiltration flow rate values $Q_{UF1}$ and $Q_{UF2}$ which correspond to the transmembrane pressure values $TMP_1$ and $TMP_2$ used as references in the kidney shown in FIG. 1.

The final difference between this second kidney and the first kidney is that it is the sterile liquid circulation pump 13 which is servo-controlled by the control unit 24 on the basis of the comparison it performs between the desired weight loss rate $Q_{WL}$ and the real weight loss rate as calculated from the data provided by the scales 31 and 32, with the throttle member 30 being independently adjusted by other means.

The kidney shown in FIG. 2 operates as follows. When the ultrafiltration flow rate reaches $Q_{UF1}$, switching between hemodiafiltration and hemofiltration modes is controlled as a function of a timing sequence. To this end, two durations $T_1$ and $T_2$ corresponding respectively to the two treatment modes are initially stored in the memory of the control unit 24, with the doctor being able to obtain optimum purification efficiency for each patient by a judicious choice of these two durations and of the ratio between them.

The present invention is not limited to the two embodiments described above, and variants may be provided.

Thus, the source of sterile liquid may be constituted by a prepackaged bag of solution or by a container designed to be filled with a liquid prepared extemporaneously. The artificial kidney may also comprise several independent sources of sterile liquid connected respectively, by means of ducts 14, 15, 16, to the second compartment 3 of exchanger 1 and to bubble traps 8, 9. The liquid may be a conventional dialysis solution containing all blood electrolytes, or it may be a solution having no buffer agent (sodium bicarbonate). Under such circumstances, the buffer agent may be perfused to compensate for the diffusion and convection losses that occur in the exchanger.

In the embodiment of FIG. 2, the throttle member 30 may be replaced by a pump controlled by the control unit 24 as a function of the pressure that exists in the compartment 2 of the exchanger 1. Since in this particular embodiment the pressure in the compartment 3 depends only on the relative positions of the containers 11 and 20 and on the head losses in the ducts, this pressure is constant for a given arrangement of the kidney, and the pressure in the compartment 2 is thus representative of the transmembrane pressure in the exchanger. Under such circumstances, the flow rate of the pump 13 is not regulated, but is initially adjusted to a given value.

Also, the artificial kidney shown in FIG. 1 can be operated in the mode adopted for the kidney shown in FIG. 2 in which alternation between hemofiltration and hemodiafiltration treatments is controlled as a function of a timing sequence. The pressure sensors 25 and 26 are then used to verify that the pressures on either side of the membrane do not exceed safety thresholds.

Moreover, although the operation of the kidney of the invention is described for implementing treatment by hemodiafiltration and treatment by hemofiltration with perfusion of a substitution liquid in the circuit for conveying a flow of blood outside the body and downstream from the exchanger, the kidney can be used for various other types of treatment including: pure ultrafiltration with the clamps 17, 18, and 19 being closed and with the sterile liquid pump 13 being stopped; and hemofiltration with substitution liquid being perfused into the circuit for conveying blood outside the body at a point upstream from the exchanger 1, with the clamps 17 and 19 being closed and the clamp 18 open.

What is claimed is:

1. An artificial kidney, comprising:
    A blood circuit for conveying blood flow outside the human body, said blood circuit being connectable to a source of treatment liquid;
    an exchanger having two compartments separated by a semipermeable membrane, a first compartment being connected to the blood circuit, and a second compartment having an inlet connectable to a source of treatment liquid;
    means for establishing a positive transmembrane pressure between the first and second compartments of the exchanger;
    means for measuring a value representative of the transmembrane pressure in the exchanger, thereby establishing a measured value; and
    control means for causing a source of treatment liquid to be connected to the inlet of the second compartment of the exchanger when said measured value is greater than a threshold value.

2. An artificial kidney according to claim 1, wherein the threshold value is a first threshold value and the control means is also for connecting a source of treatment liquid to the blood circuit when the measured value is less than a second threshold value, lower than the first threshold value.

3. An artificial kidney according to claim 1, wherein the control means is also for alternatively connecting a source of treatment liquid to one of the inlet of the second compartment of the exchanger and the blood circuit according to a timing sequence.

4. An artificial kidney according to claim 1, wherein the means for measuring a value representative of the transmembrane pressure in the exchanger includes pressure sensors connected to each of the first and second compartments of the exchanger.

5. An artificial kidney according to claim 1, wherein the means for measuring a value representative of the transmembrane pressure in the exchanger includes scales for weighing a treatment liquid source and the liquid flowing out of the exchanger, said value being the ultrafiltration flow rate calculated from data provided by the scales.

6. An artificial kidney according to claim 1, wherein a source of treatment liquid is connectable to the blood circuit either upstream or downstream of the exchanger.

7. An artificial kidney according to claim 1, wherein the means for establishing a transmembrane pressure in the exchanger includes a pump placed on a duct connected to an outlet of the second compartment of the exchanger.

8. An artificial kidney according to claim 1, further including means for measuring the difference between the flow of treatment liquid flowing from a source of treatment liquid and a flow of waste liquid exiting the second compartment of the exchanger.

9. An artificial kidney according to claim 8, wherein the source of treatment liquid includes a container and the means for measuring the difference between the flows of treatment liquid and waste liquid includes scales for weighing a first container of treatment liquid and a second container for collecting the waste liquid.

10. An artificial kidney according to claim 8, wherein the control means controls the means for establishing a transmembrane pressure in the exchanger as a function of a comparison between a measured difference and a desired difference between the flows of treatment liquid and waste liquid.

11. An artificial kidney according to claim 1, wherein the blood circuit and the second compartment of the exchanger are connectable to the same source of treatment liquid.

12. The artificial kidney according to claim 1, wherein the threshold value is a first threshold value, and the control means is also for disconnecting of the source of treatment liquid from the inlet of the second compartment of the exchanger when the measured value is less than a second threshold value lower than the first threshold value.

13. An artificial kidney according to claim 1 wherein the threshold value corresponds substantially to a maximum ultrafiltration rate of the artificial kidney.

14. A method for controlling an artificial kidney, comprising the steps of:
    establishing a positive transmembrane pressure between first and second compartments of an exchanger having two compartments separated by a semipermeable membrane, the first compartment being connected to a blood circuit for conveying blood outside of a human body, and the second compartment having an inlet connectable to a source of treatment liquid;
    measuring a value representative of the transmembrane pressure in the exchanger to thereby establish a measured value;
    comparing said value with a threshold value; and
    flow connecting a source of treatment liquid with the inlet of the second compartment of the exchanger when the measured value is greater than the threshold value.

15. A method according to claim 14, wherein the threshold value is a first threshold value, the method further comprising the steps of comparing the measured value with a second threshold value, the second threshold value being less than the first threshold value, and flow connecting a source of treatment liquid with the blood circuit when the measured value is less than the second threshold value.

16. A method according to claim 14, further comprising the step of alternating, in a timing sequence, a connection of the source of treatment liquid between the inlet of the second compartment of the exchanger and the blood circuit when the measured value has reached the threshold value.

17. A method according to claim 14, further comprising the stems of measuring a difference between a flow of treatment liquid flowing from a source of liquid and the flow of waste liquid flowing from the second compartment of the exchanger, and controlling the transmembrane pressure as a function of a comparison between the measured difference and a desired difference in flow of treatment liquid and waste liquid.

18. The method according to claim 14, further comprising the step of comparing the measured value with a second threshold value lower than the first threshold value, and disconnecting the source of treatment liquid from the inlet of the second compartment of the exchanger when the measured value is less than the second threshold value.

19. A method according to claim 14 wherein the threshold value corresponds substantially to a maximum ultrafiltration rate of the artificial kidney.

20. A method for controlling an artificial kidney operable in both hemofiltration and hemodialysis modes of operation, the method comprising the steps of:

selecting an upper threshold transmembrane pressure value at which point the artificial kidney will switch from functioning in a hemofiltration mode to a hemodialysis mode, the transmembrane pressure value corresponding to a pressure differential across a membrane in a dual compartment exchanger, a first compartment of the exchanger being connected into an extracorporeal blood circuit and the second compartment being selectively connectable to a source of treatment liquid;

measuring a transmembrane pressure of the exchanger; and flow connecting the second compartment with the treatment liquid source when a measured transmembrane pressure reaches the selected upper threshold value.

21. A method according to claim 20 further comprising the steps of selecting a lower threshold transmembrane pressure value at which point the artificial kidney will be switched from functioning in a hemodialysis mode to a hemofiltration mode, and connecting a treatment liquid source to the blood circuit when a measured transmembrane pressure reaches the lower threshold value.

22. A method according to claim 20 wherein the step of selecting the upper threshold value includes the substeps of entering a desired blood flow rate and a desired weight loss rate into a control unit programmed to calculate the upper threshold value.

23. The method according to claim 20 wherein the hemodialysis mode of operation is hemodiafiltration.

* * * * *

UNITED STATES PATENT AND TRADEMARK OFFICE
CERTIFICATE OF CORRECTION

PATENT NO. : 5,366,630
DATED : November 22, 1994
INVENTOR(S) : Jacques Chevallet It is certified that error appears in the above-indentified patent and that said Letters Patent is hereby corrected as shown below:

Claim 17, column 8, line 62, change "stems" to --steps--.

Signed and Sealed this

Thirty-first Day of January, 1995

Attest:

BRUCE LEHMAN

Attesting Officer     *Commissioner of Patents and Trademarks*